(12) United States Patent
Lincoln

(10) Patent No.: US 7,417,119 B2
(45) Date of Patent: Aug. 26, 2008

(54) NANOSCALE ARRAY BIOMOLECULAR BOND ENHANCER DEVICE

(75) Inventor: Patrick Denis Lincoln, Woodside, CA (US)

(73) Assignee: SRI International, Menlo Park, CA (US)

(*) Notice: Subject to any disclaimer, the term of this patent is extended or adjusted under 35 U.S.C. 154(b) by 25 days.

(21) Appl. No.: 11/333,951

(22) Filed: Jan. 17, 2006

(65) Prior Publication Data

US 2007/0167609 A1 Jul. 19, 2007

(51) Int. Cl.
*C07K 1/00* (2006.01)

(52) U.S. Cl. .................. 530/350; 977/789; 977/793

(58) Field of Classification Search ............ 977/789, 977/793; 530/350
See application file for complete search history.

(56) References Cited

U.S. PATENT DOCUMENTS

| | | | | |
|---|---|---|---|---|
| 5,130,105 A * | 7/1992 | Carter et al. | ............ | 422/215 |
| 5,221,410 A * | 6/1993 | Kushner et al. | ............ | 117/70 |
| 5,419,278 A * | 5/1995 | Carter | ............ | 117/206 |
| 6,038,060 A * | 3/2000 | Crowley | ............ | 359/328 |
| 6,060,724 A * | 5/2000 | Flory et al. | ............ | 257/24 |
| 6,069,380 A * | 5/2000 | Chou et al. | ............ | 257/315 |
| 6,117,567 A * | 9/2000 | Andersson et al. | ............ | 428/690 |
| 6,256,767 B1 * | 7/2001 | Kuekes et al. | ............ | 716/9 |
| 6,267,935 B1 * | 7/2001 | Hol et al. | ............ | 422/245.1 |
| 6,433,355 B1 * | 8/2002 | Riess et al. | ............ | 257/40 |
| 6,445,006 B1 * | 9/2002 | Brandes et al. | ............ | 257/76 |
| 6,445,126 B1 * | 9/2002 | Arai et al. | ............ | 313/504 |
| 6,528,020 B1 * | 3/2003 | Dai et al. | ............ | 422/98 |
| 6,781,166 B2 * | 8/2004 | Lieber et al. | ............ | 257/211 |
| 6,835,591 B2 * | 12/2004 | Rueckes et al. | ............ | 438/99 |
| 7,049,626 B1 * | 5/2006 | Chen | ............ | 257/9 |

(Continued)

OTHER PUBLICATIONS

Vaseahta et al., Nanostructured and Nanoscale Devices, Sensors, and Detectors, Jul. 1, 2005, Elsevier, Science and Technology of Advanced Materials 6 (2005) 312-318.*

(Continued)

*Primary Examiner*—Robert M. Kunemund
*Assistant Examiner*—G. Nagesh Rao
(74) *Attorney, Agent, or Firm*—Deborah Neville

(57) ABSTRACT

The invention teaches the use of an addressable nanoscale device to create a programmable substrate useful in selectively attracting proteins, nucleating protein crystals and growing protein crystals of a size amenable to diffraction analysis. Further taught is the use of nanoscale assemblies to create charge patterns, where such charge patterns are useful in purifying, nucleating or crystallizing protein molecules. Charge extension moieties, including water, are taught. The invention provides rapid and efficient identification, purification and detection of proteins and protein-related complexes.

6 Claims, 10 Drawing Sheets

U.S. PATENT DOCUMENTS

| | | | |
|---|---|---|---|
| 7,112,241 B2 * | 9/2006 | Sha | 117/68 |
| 7,129,554 B2 * | 10/2006 | Lieber et al. | 257/414 |
| 7,256,466 B2 * | 8/2007 | Lieber et al. | 257/414 |
| 2002/0117659 A1 * | 8/2002 | Lieber et al. | 257/14 |
| 2003/0173595 A1 * | 9/2003 | Kuekes | 257/202 |
| 2005/0095577 A1 * | 5/2005 | Yang et al. | 435/4 |
| 2005/0117441 A1 * | 6/2005 | Lieber et al. | 365/232 |
| 2005/0265648 A1 * | 12/2005 | Roitman et al. | 385/12 |
| 2007/0166816 A1 * | 7/2007 | Campbell et al. | 435/288.4 |
| 2007/0167609 A1 * | 7/2007 | Lincoln | 530/350 |

OTHER PUBLICATIONS

DeHon et al., Nanowire-Based Sublithograhic Programmable Logica Arrays, Feb. 22-24, 2004, Otabined from DeHon's public web-library at Cal-Tech.*

DeHon et al., Sub-Lithographic Smeiconductor Computing Systems, Jul. 30, 2003, Obtained from DeHon's public web-library at Cal-Tech, Appeared in HotChips 15, Stanford University, Aug. 17-19, 2003.*

* cited by examiner

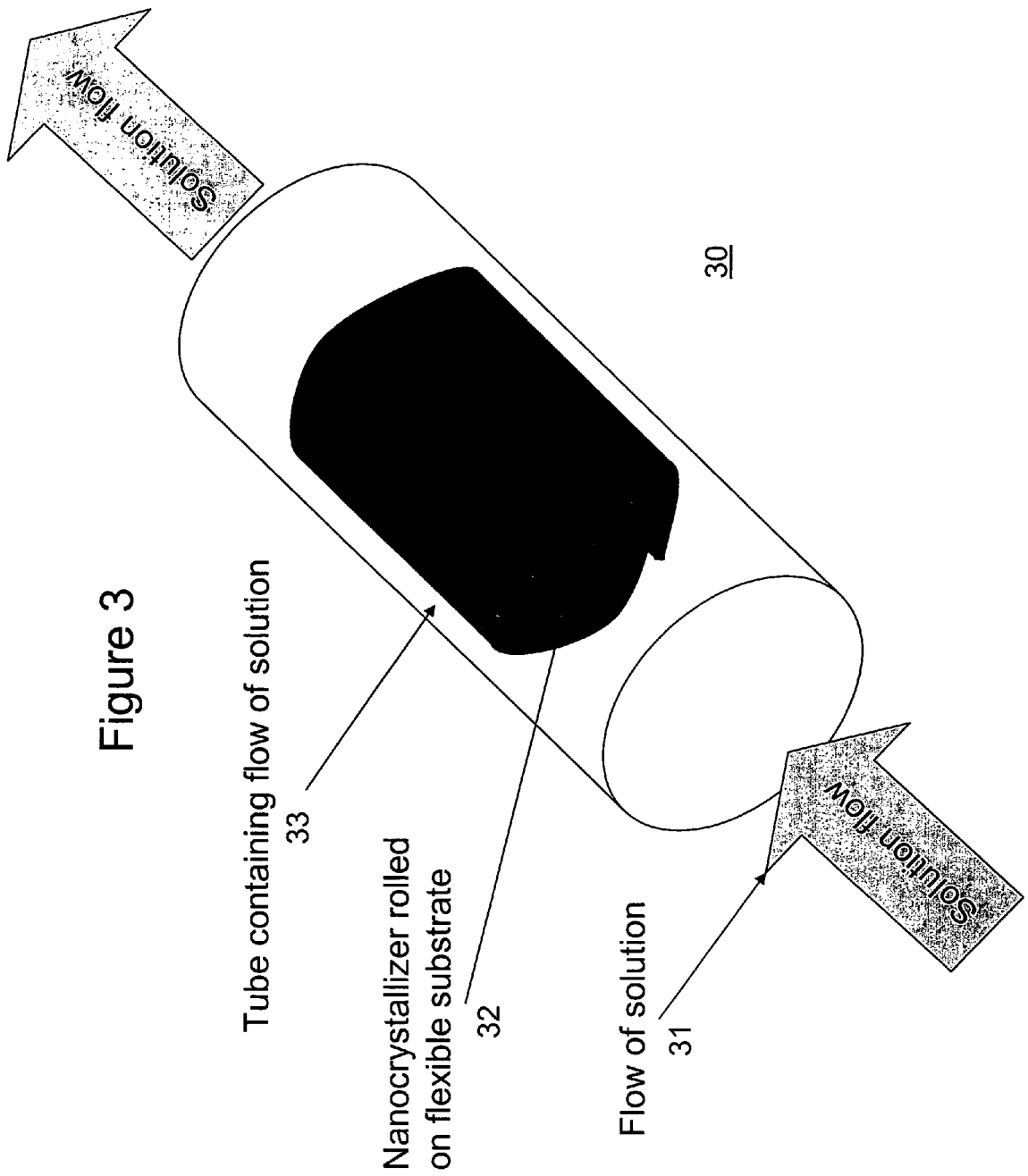

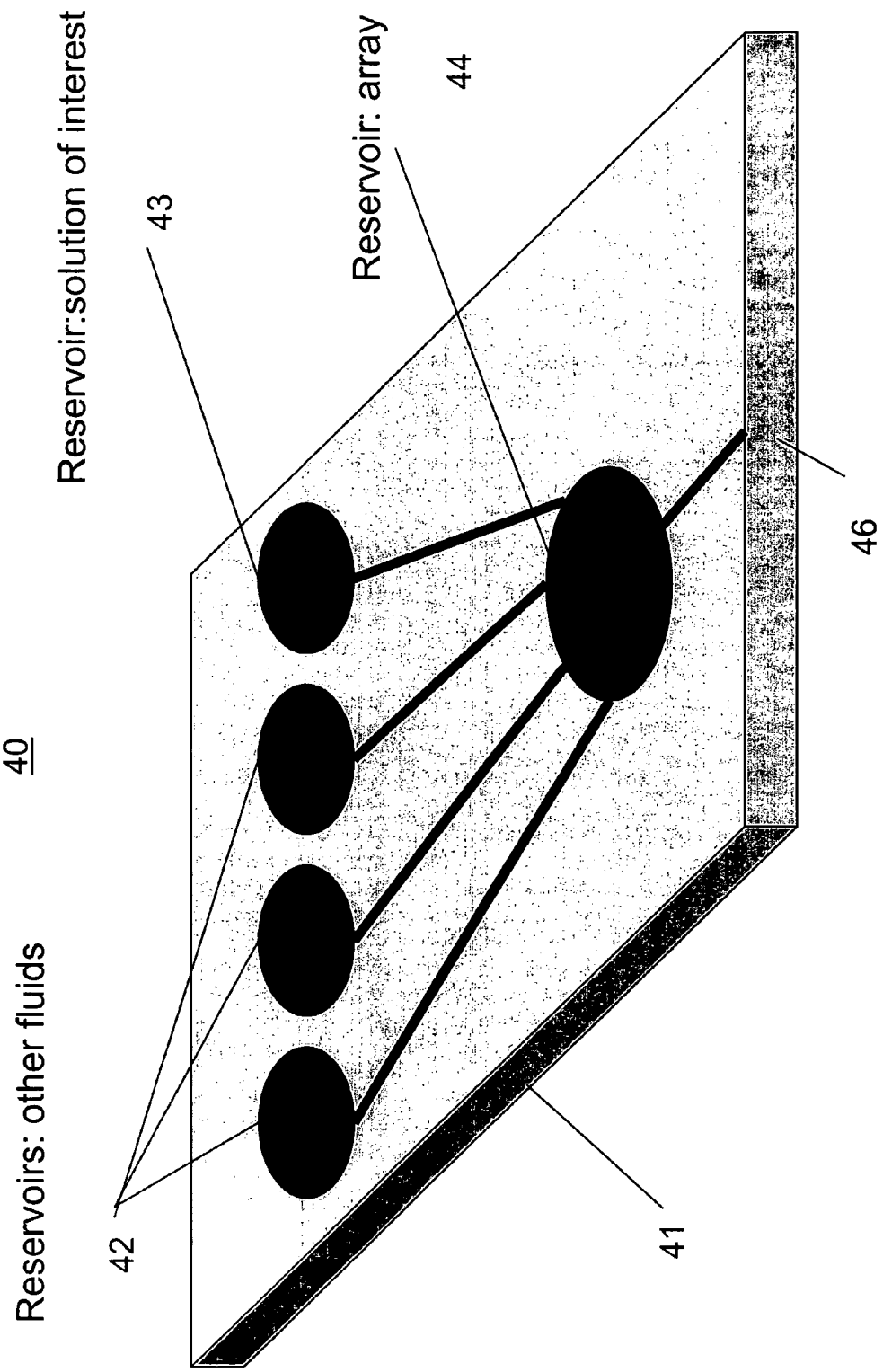

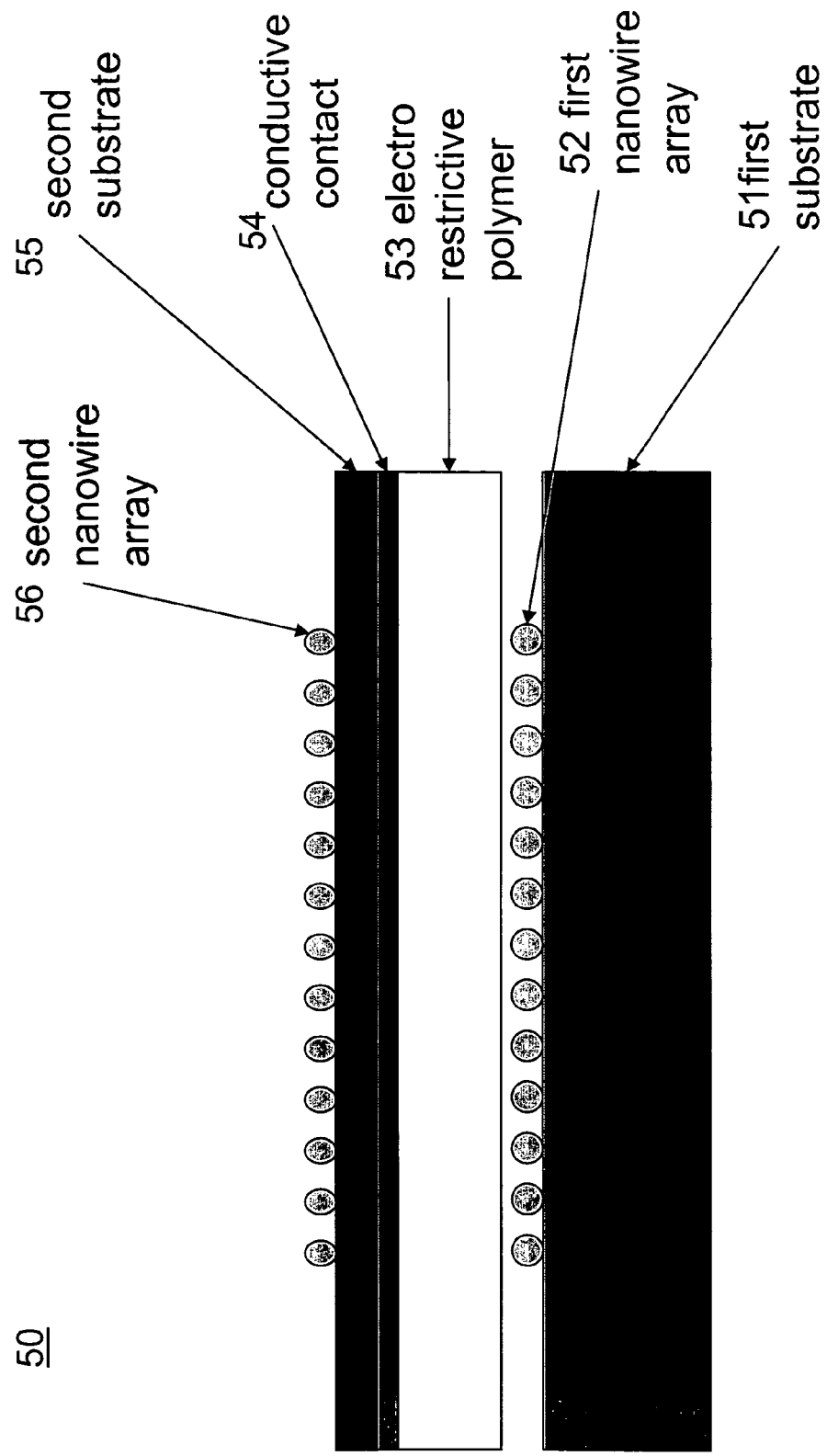

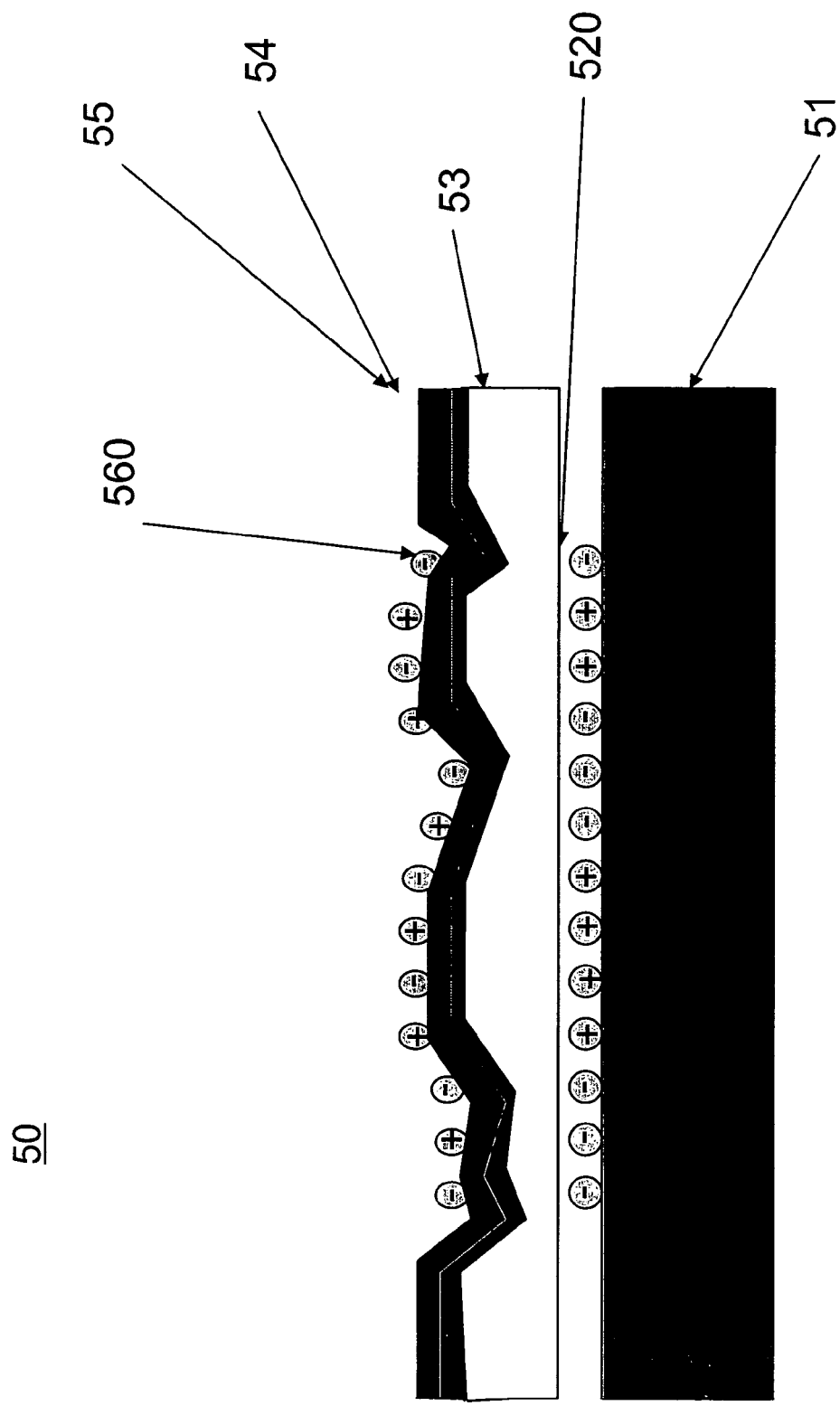

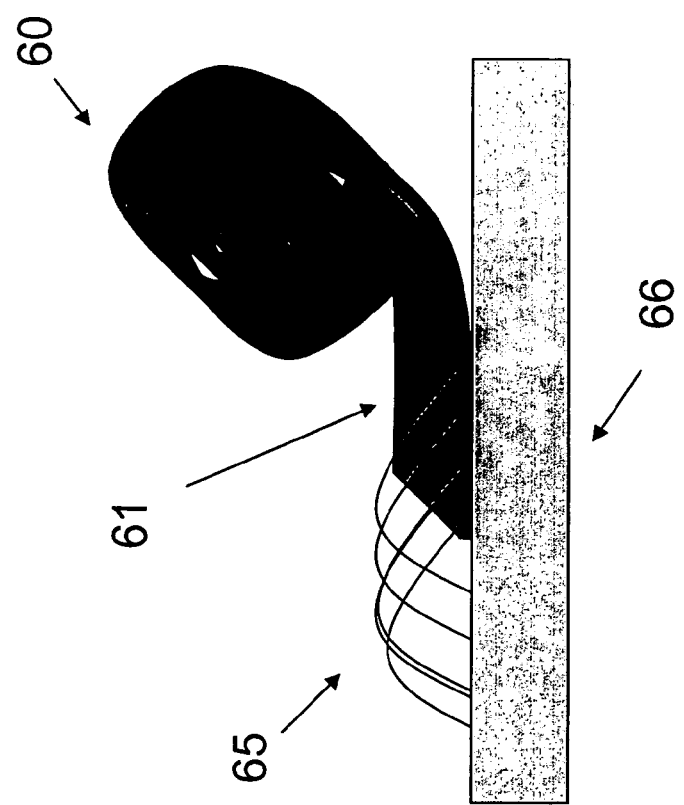
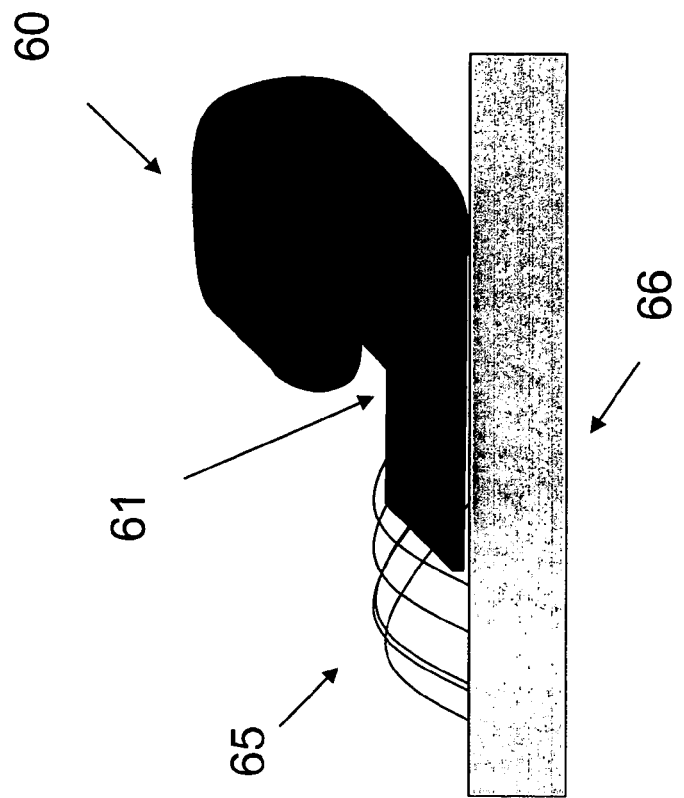

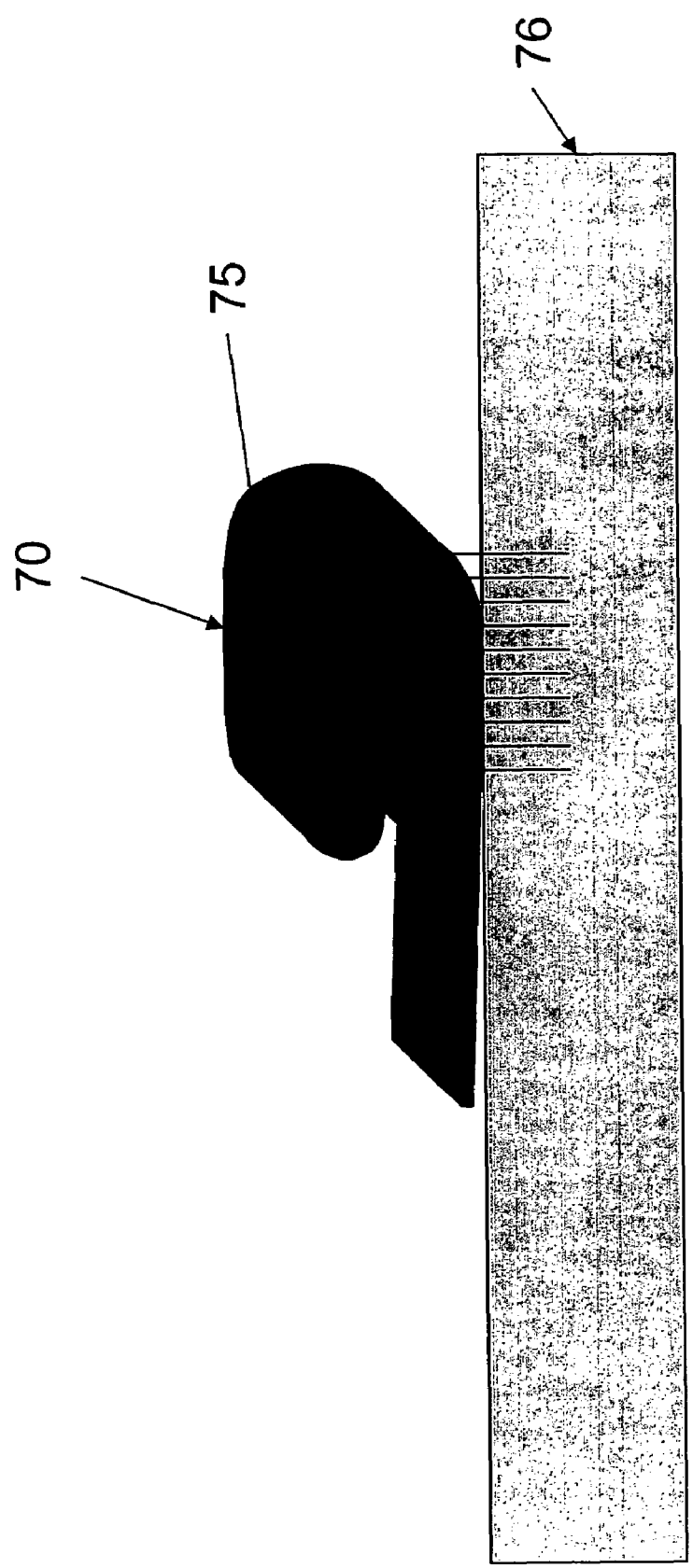

NANOSCALE ARRAY BIOMOLECULAR BOND ENHANCER DEVICE

RELATED CASES

Not applicable.

GOVERNMENT FUNDING

Not applicable.

TECHNICAL FIELD

Biomolecular engineering, and in particular protein bonding and crystallization

BACKGROUND

There are about 100,000 different proteins expressed in eukaryotic systems. Protein structural models are a unique source of information: location and properties of binding sites in toxins; domain structure of lipoproteins; molecular contact and recognition. Generating correct and detailed structural models of proteins is aided by the ability to obtain and analyze a protein in its crystal form.

Proteins are macromolecules (heteropolymers) made up from 20 different amino acids, also referred to as residues. For proteins below about 40 residues the term peptide is frequently used. A certain number of residues is necessary to perform a particular biochemical function, and around 40-50 residues appears to be the lower limit for a functional domain size. Protein sizes range from this lower limit to several hundred residues in multi-functional proteins.

Proteins can be several hundred residues long and fold into a 3-dimensional structure. It is therefore quite understandable that protein molecules have irregular shapes and are not ideally suited to be stacked into a periodic lattice, i.e., a crystal. Protein crystals are thus very fragile, soft and sensitive to environmental variations. Protein crystals contain on average 50% solvent, mostly in large channels between the stacked molecules of the crystal. The interactions holding the molecules together are usually weak, hydrogen bonds, salt bridges, and hydrophobic interactions.

The structures of many important proteins remain a mystery simply because researchers are unable to obtain crystals of high enough quality or large enough size. Generally, for useful measurements to be obtained, crystals must have dimensions of approximately 0.3 mm to 1.0 mm, and the protein molecules must be arranged in an orderly, repeating pattern.

In order to obtain a crystal, the protein molecules must assemble into a periodic lattice. To bring the protein molecules into close association so that nucleation may occur, one typically starts with a solution with a high protein concentration (2-50 mg/ml) and adds reagents that reduce the solubility close to spontaneous precipitation. By slow further concentration, and under conditions suitable for the formation of a few nucleation sites, small crystals may start to grow. Often many conditions have to be tried to succeed. This is usually done by initial screening, followed by a systematic optimization of conditions. Crystals should to be sub-mm range in each direction to be useful for conventional diffraction experiments.

Other techniques for growing protein crystals, such as 'sitting drops', 'dialysis buttons', and 'gel and micro batch' techniques are known in the art. Devices for promoting crystallization include the hanging-drop, sitting-drop, sandwich-drop, dialysis, micro batch or microtube batch devices (U.S. Pat. Nos. 4,886,646, 5,096,676, 5,130,105, 5,221,410 and 5,400,741; Pav et al., Proteins: Structure, Function, and Genetics, 20, pp. 98-102 (1994); Chayen, Acta. Cryst., D54, pp. 8-15 (1998), Chayen, Structure, 5, pp. 1269-1274 (1997), D'Arcy et al., J. Cryst. Growth, 168, pp. 175-180 (1996) and Chayen, J. Appl. Cryst., 30, pp. 198-202 (1997), incorporated herein by reference). Microseeding may be used to increase the size and quality of crystals.

In iterative drug design, crystals of a series of protein or protein complexes are obtained and then the three-dimensional structure of each crystal is solved. Such an approach provides insight into the association between the proteins and compounds of each complex.

Notwithstanding the variety of methods practiced, what are constantly sought are faster, less expensive methods of crystallizing biomolecules, and, in particular, proteins.

Nucleation requires higher levels of saturation than those associated with metastable phases amenable to crystal growth. An environment that favors a higher local concentration of macromolecules may lower the energy barrier for nucleation. Compositionally modulated superlattices have been identified which act as potent and highly specific catalysts for the nucleation of many different protein crystals. (See "Nanoengineered Surfaces for the Epitaxial Nucleation of Protein Crystals", Robert Haushalter and Ted X. Sun, Parallel Synthesis Technologies and Alexander McPherson, Univ. of California, Irvine, Calif.).

What is needed is a means of providing an environment that favors a high local concentration of the macromolecules of interest, and thereby fostering nucleation and subsequent crystallization. What is needed are ways to bring protein molecules or residues in close association under conditions so as to promote the weak bonding necessary for protein crystallization. Further, what is needed is a rapid means of calibrating conditions for a high through-put protein purification, nucleation and/or crystal growth.

What is also needed is a "bottoms up" nanoscale means to promote protein-protein bonding and crystal growth. What is also needed is a controllable nanoscale environment to assemble biomolecules, including proteins, in periodic lattice formations. What is further needed is the ability to grow crystals suitable for diffraction analysis on a programmable nanoscale array.

What is also desired is a method for creating a surface designed for seeding organic crystals and especially protein crystals. Further desired is a means to refine and purify proteins in mixtures and solutions. What is needed are purifying devices and methods that facilitate protein nucleation, protein crystallization and other protein identification and testing steps, as well as refining or purifying protein-based drugs or drug-precursors.

BRIEF SUMMARY

The invention teaches the use of an addressable nanoscale array assembly on a substrate to program a charge pattern upon a surface of the nanoscale array. The invention provides a device allowing for the charge bearing surface to be exposed to a solution containing a biomolecules of interest. The charge pattern upon the surface is useful in causing close association of charge bearing biomolecules. Such close association provides, depending on a number of factors, weak bonding between the molecule of interest and the surface, as well as bonding among other instances of the molecule of interest, that is, inter-molecular bonding. The device may be used for purification of a molecule or protein of interest, or nucleation or seeding of protein crystals. The invention provides for protein crystal formation of a variety of sizes ranging from seed crystal size to protein crystals of sizes amenable to diffraction analysis in a high throughput, rapid and inexpensive manner.

The invention employs nanoscale addressable arrays (with myriad cross points) to create programmable charge patterns—portions of negative, positive or neutral charge. Owing to the charge attraction exerted on charged portions of protein molecules, the nanoscale arrays charge patterns may be configured to attract molecules with certain charge characteristics. Moreover, the addition of water (or other suitable hydrophobic or hydrophilic charge extension moiety or moieties) amplifies the effective range of charge and facilitates proximity and attraction of a variety of molecules of interest. The molecules of interest may be any biomolecules, such as a known protein being purified, nucleated or crystallized or an unknown protein being characterized.

What is also provided is a method and device for producing and harvesting protein crystals of a variety of sizes. By producing nucleated protein crystals, such crystals can be harvested and used to grow bigger crystals. In alternative embodiments, protein crystals of a size that may be amenable to analysis for structural determination or protein identification may also be grown.

The inventive device also provides a means to refine and purify mixtures and solutions. In one embodiment, the addressable nanoscale array device is positioned within a tube-like housing (or tube) or cylinder. A solution containing molecules of interest may be flowed through the tube. The length of the cylinder may be varied, as can the diameter, and the arrangement of the charge pattern surface on the nanoscale array assembly within the tube. The charge pattern on part or all of the charge bearing surface of the nanoscale array assembly may be dynamically altered. For instance, the charge can be reversed to release molecules, which can then be collected by flushing through the tube and collecting the effluent. The charge pattern can also be manipulated to direct growth of the molecule of interest.

Also provided is a multi layer nanoscale assembly array that both provides the topography of the surface (bottom or outermost layer) as well as the charge pattern (upper or innermost layer).

The invention also provides addressable arrays on a suitably transparent or transmissive polymer as a substrate or array bearing material, where the protein associations encouraged by the surface design can be optically or otherwise examined without transfer of the proteins that are bound to the surface.

Other advantages, novel features, and objects of the invention will become apparent from the following detailed description of the invention when considered in conjunction with the accompanying drawings, which are schematic and which are not intended to be drawn to scale. In the figures, each identical or nearly identical component that is illustrated in various figures is represented by a single numeral. For purposes of clarity, not every component is labeled in every figure, nor is every component of each embodiment of the invention shown where illustration is not necessary to allow those of ordinary skill in the art to understand the invention.

BRIEF DESCRIPTION OF THE DRAWINGS

FIG. 3 depicts application of a device according to the present invention.
FIG. 4 depicts an alternate embodiment of the invention.
FIGS. 5a and 5b inclusive depict an alternate embodiment.
FIGS. 6a and 6b each depict a multilayer (folded and rolled, respectively) array bearing sheet electrically connected to a logic device.
FIG. 7 depicts a capacitively coupled multi layer array bearing sheet.

DETAILED DESCRIPTION OF THE PREFERRED EMBODIMENT

INTRODUCTION. This section begins with some preliminary concepts, then the preferred embodiment is described, followed by a discussion of the components of the preferred embodiment. Definitions are placed at the end of this section so as to facilitate the flow of the description.

PRELIMINARY CONCEPTS. Nanoscale devices can be self assembled into periodic lattices. Nanowires can form programmable cross bar arrangements (see U.S. Pat. No. 6,586,965 to Keukes, incorporated be reference) Nanoscale arrays can form bistable switches (on/off) and can attract molecules (Leiber et al., US published application 20050117441, incorporated by reference). Many means have been described of fabricating and assembling nano-arrays, including self-assembled monolayer patterns (Leiber, US publication no. 20020117659, incorporated by reference).

The present invention applies a novel approach to employing a nanoscale addressable array to produce a charge pattern to cause close association of protein molecules. Depending on a number of factors, such close association may effect a purification of a protein of interest, or may result in crystal nucleation or crystal seeding. Moreover, the invention provides a charge extension moiety, such as water, to extend the charge pattern from the surface of the nanoscale array into a predetermined region.

Figure 1A:
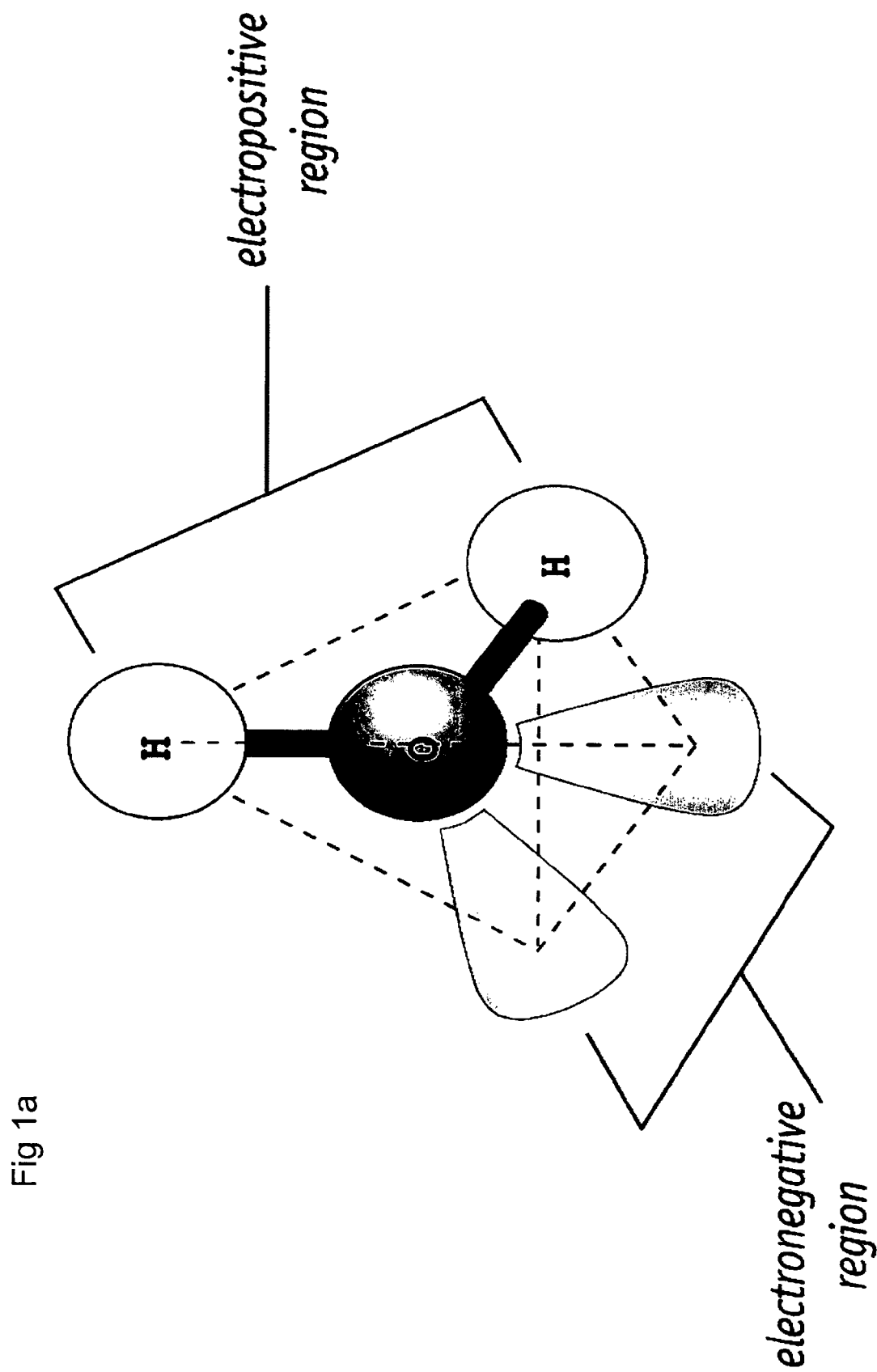
FIG. 1a depicts a water molecule and its charged regions.
Figure 1B:
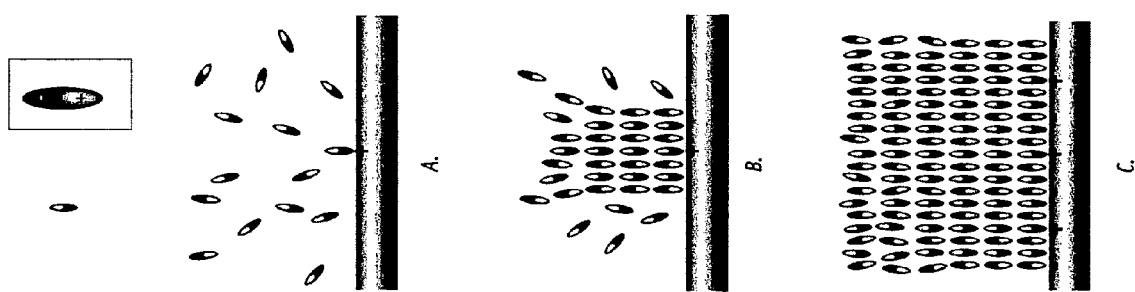
FIG. 1b alignment of water molecules in relation to charged surface.
Figure 1C:
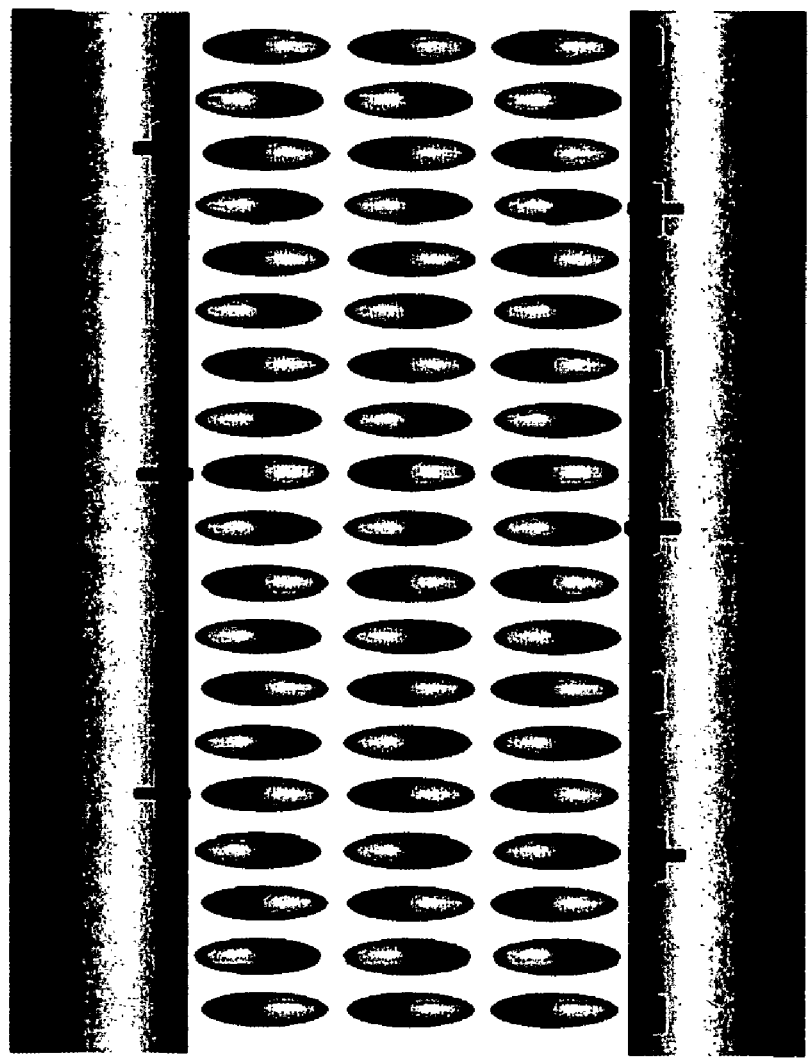
FIG. 1c depicts water alignment proximal to a charged surface.

FIG. 1a conceptually depicts the charged regions of a water molecule 10: electro-positive 12 and electro-negative 14. FIGS. 1b and 1c conceptually depict how the electronegative and electropositive regions of molecules such as water align in the presence of a charged surface 16.

Water molecules align in the presence of a charge and assume two distinct patterns, clathrate or layered, depending on whether molecules are near a hydrophobic surface or near a hydrophilic surface, respectively (see *Cells, Gels, and The Engines of Life* by Gerald H. Pollack, Ebner & Sons, Seattle, Wash.). The pattern of water molecules responding to a surface charge pattern effectively extends the pattern into a three dimensional space. Thus, water is considered for the purposes of this invention as a charge extension means. As explained further below, the charge pattern extending into a fluid interior is a means for increasing the effective attraction of protein molecules in solution and increasing the bonding of protein molecules to the surface charge and to other instances of the molecules from the protein containing solution. Referring to FIG. 1c, one need consider the charge attracting the water molecules to be arising from a nanoscale addressable array. As discussed herein, bonding to the charge bearing surface is meant to include the surface itself as well as the extended surface by means of a charge extension means.

Figure 2:
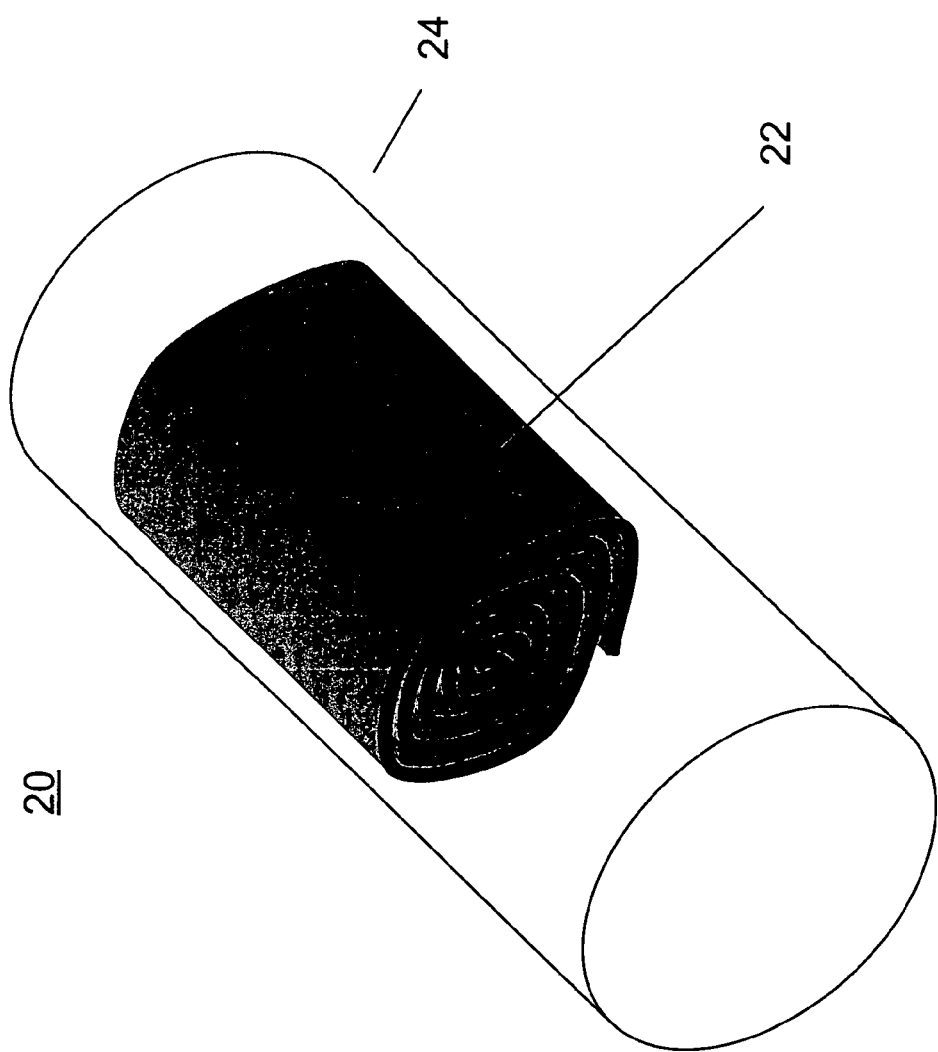
FIG. 2 depicts a device according to the present invention.

FIG. 2 shows a device 20 according to the present invention. The device 20 provides a multilayer addressable array 22 on a flexible substrate so that it may be rolled and placed within a tube-like housing 24 or fluid handling cylinder. FIG. 3 depicts a similar device along with flow of solution 31. In both FIG. 2 and FIG. 3, the nanocrystallizer substrate 22, 32 includes an addressable array of one (not depicted) or more layers of nanoscale array configured with a charge pattern. The charge pattern attracts (or repels) molecules of interest from any solution(s) introduced in the tube. In this manner, the predetermined programmable charge pattern is calculated to attract molecules from a medium exposed to the charge surface and containing molecules of interest, and to aid in the formation of a periodic lattice structure among the molecules of interest.

Thus the charge pattern may be considered a rationally designed surface that, depending on the solution or fluids introduced and the charge pattern assumed, enhances protein purification, nucleation or crystal seeding. The nanoscale programmable substrate may be a continuous sheet, may be of multiple layers, may be a series of similar patterns, or may be a progressive pattern. In short, any variation is possible along the length and within the interior of the container of the nanosubstrates. Moreover, the nanosubstrates may be statically charged or subject to dynamic charging in the course of exposure to the molecule of interest.

Consistent with the device discussed hereinabove, the invention provides a method of using a nanoscale assembly to promote bonding among molecules of interest, said method comprising the steps of programming a charge pattern on a surface of said nanoscale assembly, said charge pattern enabled by means of one or more addressable nanoscale arrays in the nanoscale assembly; and by means of a fluid medium containing at least one variety of a molecule of interest, exposing the molecule of interest to charge pattern on said nanoscale array, so as to foster bond formations between molecules of interest. In addition, the method may include adding a charge extension moiety (e.g., water) and may involve analyzing the collected molecule in situ (still attached to a substrate) or reversing or neutralizing and washing the protein aggregate, whether or not in crystal form, into an effluent for analysis, identification and/or characterization.

The invention reduces the need for engineering attachment points into the large protein molecules; it has the advantages of low cost and high efficacy in purification, crystallization and other identification or modification steps within a single device Referring to FIG. 4, an alternate embodiment (denominated a "chip" 40 for ease of reference) is one or more addressable array devices within a predetermined array reservoir 44 in a plate 41 containing fluid reservoirs 42 and solution of interest reservoir 43. As depicted in FIG. 4, the reservoirs 42, 43 have a flow channel at least with the array reservoir 44, which in turn has an aperture for outflow 46. The sequence of flow from reservoirs 42, 43 to and through the array reservoir 44 varies according to the protocol. By controlled introduction into the array reservoir 44, the conditions for growth and any subsequent processing (e.g., wash, rinse, etc.) can be carefully manipulated.

An alternate embodiment as depicted in FIGS. 5a and 5b is a multi layer array that provides the topography of the surface (bottom or outermost layer) as well as the charge pattern (upper or innermost layer). Taken together, FIGS. 5a and 5b depict an alternate embodiment 50 wherein at least two layers of addressable arrays form both the array surface shape and the charge pattern. A first substrate 51 bears a first nanoscale addressable array layer 52 which in turn bears an electrorestrictive polymer layer 53, a conductive contact layer 54, a second substrate 55 and a second addressable array layer 56.

FIG. 5b depicts the embodiment as in FIG. 5a wherein charge patterns are imposed on the first and second addressable array layers 52, 56 are modified so as to be a charge patterned first addressable array layer 520 and a charge patterned second addressable array layer 560. In the presence of a charged patterned first addressable array layer 520, the electrorestrictive polymer layer changes shape by contracting. Such a contraction pattern creates relatively lower and higher points which translate into wells and plateaus in the regions of the second addressable array layer 56, 560. Thus, proteins attracted to the charge patterned second array layer 560 can be oriented in wells created by the charge patterned first array layer 520

In cases where some or all of the substrates bearing addressable arrays are transparent polymer, the protein associations encouraged by the surface design can be optically examined without transfer of the proteins. The simplicity and economy of this one device to both capture and examine proteins and protein crystals permits heretofore unexpected speed in high throughput applications.

To obtain seed crystals suitable for X-ray diffraction, iterations on nanoscale seeding in a progressively larger growth area may be performed. According to the invention, any addressable array on a substrate could initially define a region suitable for, say, several dozen molecules as may characterize nucleation. By rearranging the charge pattern, the region could expand to include progressively larger areas, and additional deposition of protein solution may be indicated to feed crystal growth. Moreover, it may be useful to exploit a flexible array surface to gradually increase or decrease the curvature of the array substrate, or otherwise manipulate the shape to further enhance desired crystal proportions. In this manner, it may be possible to obtain the large single crystal useful in classic diffraction analysis.

Collection and Seeding. The protein of interest may be released from the addressable array surface simply by a neutralization of the attractant charge. Alternatively, an appropriate fluid wash may gently slough the protein molecules off the array. In an alternate embodiment, the protein may be processed without detaching it from the array surface. In cases where the protein structure will be used to further seed larger crystals, the array surface or a small portion of a large array surface may be cut and inserted into, for example, a hanging drop or other crystallization technique.

The invention is contemplated to include both reusable nanoscale arrays (where after harvesting of the seed crystals or protein, the array may be rinsed and re-used) and disposable array devices (where perhaps biohazard dictates single use). Pre-calibrated diagnostic chips or other pre-packaged arrays may also be usefully constructed using the inventive device. So too the transparent crystallizer which may become the substrate of an optical characterization process (a combined crystallization—analysis chamber) is apparent to one of skill in the relevant art. Whether for classic diffraction or for yet to be popularized nano diffraction analysis, the nanoscale array crystallizer composed of transparent elements may be remarkably efficient and economical.

Supplemental Description. At this point we provide additional background useful to practicing the invention taught herein.

Assembling the Array. The invention teaches an addressable nanoscale array operable to adopt a predetermined charge pattern, thereby creating a surface designed to enhance protein nucleation and protein crystal formation. Any of the methods discussed herein above, or otherwise known, for creating addressable nanoscale arrays are suitable. One array assembly method is set forth below.

Nanoscale devices. In one embodiment, silicon nanowires are used as the nanoscale devices. Various methods of nanowire production exist, and this invention is not limited as to the manner in which nanowires are produced. Typically the nanowire diameters are of about 3 to 50 nanometers; wire length about 10 to 100 microns. An array consists of about 1,000×1,000 nanowires, or a plurality of electrically connected nanoscale devices providing the functional equivalent of 1,000×1000 nanowires.

In one embodiment, the nanowire for the invention is a core-shell (Si inner, Ge outer) and the array would include a first layer of conductive wires, and a second layer of the Si-Ge core shell wires. Other compound semiconductor materials including Gallium Arsenide, GaAs, and Indium Phosphide, InP, can also be used. CdS nanowires, $Cu_2S$/CdS core-shell structures, $Cu_2S$ with Au nanoparticles and other combinations can also be used.

Transmissive and transparent material. Any material transmissive of a radiant energy may be selected. In one embodiment, the transparent material is a bi-axial oriented polyethylene terephthalate (BOPET) polyester film. The transparent medium is provided in sheets, and the sheet thickness can vary. Individual sheets may be thin (about 100 nanometers) or of a thickness three or more time greater: approximately 300 or more nanometers. In one embodiment, the inter-sheet and the inter-wire distance ideally are close to being equal.

Array assembly method. A general approach for depositing addressable arrays on a sheet is described as follows. First, a sheet is selected. The preferred method of getting the nanoscale devices parallel to a first surface of a given polymer sheet is that used to create a Langmuir-Blodgett (LB) film. An LB film is a monolayer, a set of monolayers, or a multilayer deposited from liquid onto a solid substrate wherein the resulting film properties are controllable. As applied to this invention, the next two steps are: a first swipe of a sheet through a suspension of nanowires or nanoscale devices whereby a first layer of nanoscale devices are deposited on the mylar surface in a parallel alignment; and a second swipe through such a suspension, orienting the sheet at a rotation from the first swipe, resulting in a second layer in crossbar formation with respect to the first layer. The variations to this general method of nanodevice deposition and crossbar formation will be apparent to those of skill in the relevant art, and are included in the invention as taught herein.

The two nanodevice layers in cross bar formation comprise an addressable array. Once the array is formed, if only a single sheet is to be used, then the next step is connection to a logic device. Such connection may be accomplished with known lithographic techniques, and small-scale wire leads from the array to a logic device which, in turn, preferably connects to a recording media such as flash memory or hard disk.

In the multilayer embodiments, the step of stacking sheets or folding a sheet or sheets to produce any number of layers may be performed before connectivity to a logic device.

Folding and Rolling. It is apparent that a sheet of 100 nanometers thickness and a square meter in size, folded ten times results in a cube 1 mm thick with 1,000 layers of array-bearing sheets. Alternatively, a sheet can be rolled or folded in one direction and sliced at 1 mm intervals, yielding 1 mm×1 mm×1 mm shapes. Cube, ellipse or cylinder: no shape requirement need be imposed. A sphere or any other shape may be used; at present a cube is preferred. In an alternate embodiment, layers are stacked in a skewed fashion, that is to say, aligned at an offset or otherwise adjusted in orientation so as to reduce shadow effects. Other ways of stacking and assembling array-bearing-sheets so as to minimize shadow and alternate sheet stacking configurations will be apparent to those of skill in the relevant art.

One can appreciate that a "roll" assembly method is fairly similar to a "fold" when considering on the order of one thousand layers. In a large scale operation the step of cutting after rolling or folding is included. Of course, one could just make one thousand or so separate layers and simply stack them up (without any explicit folding or rolling). Any and all such assembly techniques are intended to be included herein.

Connectivity. The currently preferred lithographic approach to electrically coupling the addressable array is described in U.S. Pat. No. 6,963,077, issued to inventors De Hon, et al., entitled "Sublithographic Nanoscale Memory Architecture" (incorporated herein by reference). Microscale devices, typically wires, are in connective association with the addressable array.

FIGS. 6a and 6b inclusive illustrates a multilayer embodiment of the imaging device and connectivity to a logic device. In FIG. 6a the array-bearing sheet 60 was folded, in 6b the array-bearing sheet 60 was rolled in one direction and leaving a slight tongue 61 or tag protruding from the roll in each case. A first set of microscale devices (not depicted) on the tongue 61 connects the addressable array by means of a second set of microscale devices 65 connecting the array to the logic device 66.

FIG. 7 depicts one connectivity embodiment of an array-bearing sheet in a layered formation via capacitive conductance. A first set of microscale devices 75 run down a face of the cube-formed multilayer array bearing sheet 70. The connectivity to the logic device 76 is by means of capacitive conductance. Capacitive conductance connectivity obviates the need for a second set of microscale devices and avoids the exposure to heat suffered during most conventional lithographic procedures. Standard CMOS chip pads (not depicted) are used and no-direct coupling to the array bearing substrate is needed.

Configuring the Array. One alternative method of configuring the array is to set a charge pattern at a distance consistent with one or more protein structure habits. In the case where some structure information exists, the distances between repeating charge elements may be calculated to correspond to surface hydrophobic or hydrophilic regions. In protocols where an unknown is being attracted, then a gradient may be used and, by iterative steps, an optimized pattern derived.

Solution Preparation. Those of skill in the relevant art are familiar with methods of preparing dilutions conducive to protein purification or crystal formation.

Solution Deposition. Where the embodiment is other than a "flow through" device, one alternative method of depositing the solution (fluid medium) is immersion of the array in a solution of interest, perhaps in a micro-titer plate or similar tray-like device. In the alternate embodiment depicted in FIGS. 5a and 5b, inclusive, the upper charge bearing surface may be a nano-topography including nano-wells and space in between the nano-wells. One solution dispensing option is microfluidic depositions in the nano-wells by means that are currently used in applications such as ink jet. The fluid medium may contain not only the molecule of interest, but may also contain seed crystals, or periodic lattices of the molecule of interest.

Current fluid techniques applied in inkjet approaches can be engaged in application of droplets on a nano scale array. Both the direction and amount of liquid can be controlled in each droplet by print heads such as those made by Dimatix. Using such a multiple drop approach, a range of dilutions can be automatically and repeatable deposited for large scale throughput of a protein of interest or a sample for identification or characterization.

The invention is intended to be inclusive of techniques known in the art concerning crystal growth conditions. It would be readily apparent to one of skill in the art to vary the crystallization conditions disclosed above to identify other crystallization conditions that would produce seed crystals. Such variations include, but are not limited to, adjusting pH, protein concentration and/or crystallization temperature, changing the identity or concentration of salt and/or precipitant used, using a different method for crystallization, or introducing additives such as detergents (e.g., TWEEN 20 (monolaurate), LDOA, Brji 30 (4 lauryl ether)), sugars (e.g., glucose, maltose), organic compounds (e.g., dioxane, dimethylformamide), lanthanide ions, or poly-ionic compounds that aid in crystallizations. High throughput crystallization assays may also be used to assist in finding or optimizing the crystallization condition.

Definitions: A selection of key terms as they are to be understood herein, including the specification, drawings and claims, are defined below for reader convenience. A definition in the singular includes the plural.

Addressable array: a nanoscale cross bar array as defined by Leiber et al. US publication number 20050117441 (incorporated herein by reference), which is addressable. The addressable array may be composed of nanoscale devices, such as, for example nanowires or any nanowire like devices capable of creating a charge pattern, as well as a means for connecting the nanoscale devices to microscale input/output. Some approaches for such nano-microlithography are taught in U.S. Pat. No. 6,963,077 (incorporated herein by reference) and are compatible with the device taught herein. Herein, "array" means "addressable array" unless explicitly stated otherwise.

Array-bearing sheet: any suitable material of a predetermined thickness bearing at least one addressable array, wherein said array includes some nanowire-like or other nanoscale devices capable of creating a charge pattern.

Capacitive coupling: a means for electrically connecting devices; see, e.g., "Manufacturability of Capacitively Coupled Multichip Modules", Thomas F. Knight, Ph. D. and David B. Salzman, Ph. D. 1994 IEEE pp. 605-608 (incorporated herein by reference).

Langmuir-Blodgett: a process or set of processes amenable for a wide variety of applications and particularly adaptable for depositing nanoscale devices in a crossbar array on selected sheet material.

Logic device: any device capable of operatively interacting with the addressable array and performing all or some of the functions of amplifying, storing, processing, and transmitting the output from the addressable array. Includes, but is not limited to, CMOS family of integrated circuits.

Microscale fabrication devices: microscale wires or the equivalent in conductive association with at least one addressable array.

Nano: "nano", alone or in combination with "scale" (i.e. nanoscale) or any other term, is meant to include elements of widths or diameters of less than 1.mu.m Nanowire: structures as described by Leiber USPTO publication number 20050117441 (incorporated herein by reference). A "wire" refers to any material or combination of materials having a conductivity of any semiconductor or any metal including, but not limited to nanorods, nanowires, organic and inorganic conductive and semiconducting polymers. Moreover, as used herein, "nanowire" also means any nanowire or nanowire like element, and includes but is not limited to semiconductor nanowire, nanowire core-shell structure, nanowire heterojunction, or junction between nanowire and other material, including metal or polymer. Semiconductors used include the standard list (Si, GaAs, etc.) as well as any compositions from which an addressable array may be formed. One alternative embodiment uses core-shell nanowires.

Nanoscale device: any device of nano dimensions capable of homogenously or heterogeneously participating in an addressable array. As used herein, participation is understood to mean directly or indirectly contributing to a charge pattern. A nanoscale device may be composed, in whole or in part, of nanowires.

Stack (stacking): two or more array-bearing sheets closely associated in such a manner so that conditions enabling a volumetric hologram exist; process of bringing about such an association of array-bearing sheets.

Transparent medium: any transparent material suitable for sheet formation and capable of bearing an addressable array, the preferred transparent material is a biaxially-oriented polyethylene terephthalate (BOPET) polyester film.

The present invention is not limited to given embodiments or examples. Rather, the invention is intended to include all that is described and depicted, or set forth in the attached set of claims, along with the equivalents thereto, that define possible further embodiments for a person skilled in the art.

The invention claimed is:

1. A device for promoting the bonding of molecules from a medium containing unbound molecules of interest, said device comprising:
    an addressable nanoscale array, said nanoscale array being multilayer and on a flexible substrate and wherein a charge pattern is imposable on a first surface of said addressable nanoscale array, such that the charge pattern is predetermined to selectively attract molecules from said medium and whereby, as a consequence of the attraction of the charge pattern, formation of bonds among said molecules of interest is effected.

2. A device as in claim 1 where said charge pattern is calculated to promote bonding of molecules associated with crystal growth from the molecule of interest.

3. A device as in claim 1 further comprising a surface charge pattern extension moiety to selectably extend said charge pattern imposable on said first surface.

4. A device as in claim 3 where said charge pattern is predeterminedly calculated to effect positioning of molecules, and in particular protein molecules, such that said positioned molecules are in a governable orientation relative to the device.

5. A device as in claim 4 where the device together with any associated molecule is directly amenable to analysis and where said positioned molecules are suitable for analysis without requiring change in orientation relative to or removal from the device.

6. A device as in claim 4 wherein said charge pattern is dynamically addressable.

* * * * *